(12) United States Patent
Casali

(10) Patent No.: US 11,478,229 B1
(45) Date of Patent: Oct. 25, 2022

(54) SELF-DEFENSE DEVICE

(71) Applicant: joseph Casali, Franklin Lakes, NJ (US)

(72) Inventor: joseph Casali, Franklin Lakes, NJ (US)

(*) Notice: Subject to any disclaimer, the term of this patent is extended or adjusted under 35 U.S.C. 154(b) by 0 days.

(21) Appl. No.: 17/483,606

(22) Filed: Sep. 23, 2021

(51) Int. Cl.
*F21S 9/00* (2006.01)
*A61B 10/02* (2006.01)
*F41H 9/10* (2006.01)
*F21S 9/02* (2006.01)
*F21S 10/06* (2006.01)
*G10K 5/00* (2006.01)

(52) U.S. Cl.
CPC ............ *A61B 10/02* (2013.01); *F21S 9/02* (2013.01); *F21S 10/06* (2013.01); *F41H 9/10* (2013.01); *G10K 5/00* (2013.01)

(58) Field of Classification Search
CPC .... F21S 10/06; F21S 9/02; G10K 5/00; F41H 9/10; A61B 10/02
See application file for complete search history.

(56) References Cited

U.S. PATENT DOCUMENTS

| 10,054,305 | B1* | 8/2018 | Slepack | ............ F21V 33/0064 |
| 2019/0271528 | A1* | 9/2019 | Nangunoori | ............ F41H 9/10 |
| 2021/0199410 | A1* | 7/2021 | Bogacz | ............ F41H 9/10 |

* cited by examiner

*Primary Examiner* — Y M. Quach Lee
(74) *Attorney, Agent, or Firm* — Michael J. Feigin, Esq.; Feigin and Fridman LLC

(57) ABSTRACT

A self-defense device includes a body, a self-defense spray canister within the body, a whistle coupled to the body and the canister, and a light source within the body. The body includes a longitudinal bore and a defense ring extending annularly around the body. The ring includes an upper surface, a lower surface including an abrasive area for scraping a body surface, and an interior receptacle for collecting material scraped from the body surface. The canister is disposed within the longitudinal bore and includes a nozzle for discharging the self-defense fluid. The whistle includes a mouthpiece and a housing coupled to the spray canister. The housing includes a quick release mechanism for removably attaching the housing to the body and maintaining the canister in a fixed position within the housing. The mouthpiece is pivotally connected to the housing enabling pivoting about the housing to provide access to the nozzle.

20 Claims, 6 Drawing Sheets

SELF-DEFENSE DEVICE

FIELD OF THE DISCLOSED TECHNOLOGY

The disclosed technology relates generally to a self-defense device for protecting oneself against, and deterring, attackers. More specifically, the disclosed technology relates to a combination self-defense device, colored interchangeable sleeves and a whistle for alerting people of an attacker, a spray canister for dispensing a self-defense fluid to disable or repel an attacker, a bottom striking portion, and a DNA collection device for collecting the DNA of the attacker.

BACKGROUND OF THE DISCLOSED TECHNOLOGY

Individuals often carry self-defense devices to protect themselves from attack from dangerous humans or animals. Some individuals carry weapons for self-defense. Carrying weapons for self-defense has many legal and safety risks, however, and so it is desirable to have a self-defense device which is less dangerous. Canisters of self-defense aerosol spray have become popular self-defense items. Self-defense aerosol repellent sprays such as tear gas or pepper spray are strong enough to stop an attacker from causing harm, and yet not strong enough to permanently disable or kill another individual. Thus, canisters of self-defense aerosol spray provide a less dangerous self-defense alternative to weapons.

However, while canisters of self-defense aerosol spray can ward off or disable attackers, they do not provide an alert device capability. An alert device is a device which draws attention to oneself, in the hope that if an individual is being attacked, others will be alerted and can come and help. One alert option is to carry a whistle or alarm that makes a loud noise in the presence of danger. The whistle or alarm will attract attention and hopefully help will arrive. Often a potential attacker will flee when there is the potential to draw a crowd, and if this does not occur, then the others that are drawn can help to capture or deter the attacker. But if an individual wants to use the aerosol repellent spray and also alert others to the dangerous situation, then two devices must be carried. It is not practical to carry more than one device that needs to be activated in an emergency. Thus, it is desirable to have a self-defense device which provides both an alert function and an attacker disabling function in one device, which is easy to carry and operate.

Though combined whistle and aerosol repellent spray self-defense devices have the benefit of alerting and disabling attackers, they do not provide a DNA collection capability. Indeed, although often times attackers are thwarted in their attempts to violate an individual, they are left uncaught as they either flee the scene or cannot be properly identified by the individual. Even when the attackers successfully commit a crime against individuals, they often flee the scene successfully and remain uncaught. In many instances of attack, regardless if whether the attacker is thwarted or succeeds, individuals end up struggling against the attacker and striking the attacker. Thus, there is opportunity for the individual to strike the attacker and collect DNA for purposes of providing the DNA to the authorities for further processing, identification, and capture of the attacker. Accordingly, it is desirable to have a self-defense device that not only provides an alert function and attacker disabling function, but also a DNA collection means.

SUMMARY OF DISCLOSED TECHNOLOGY

The disclosed technology provides a self-defense device including a tubular body, a self-defense spray canister disposed within the body, a whistle coupled to the body and the canister, and a light source. The body includes a first end having a first opening, a second end having a second opening, the first end opposite the second end, an outer surface, an interior surface, the outer surface opposite the interior surface, a first side, a second side, the first side opposite the second side, a longitudinal bore extending from the first end to the second end, and a defense ring extending annularly around the second end of the body and protruding outwardly relative to the body, the defense ring including an upper surface and a lower surface, the upper surface perpendicular to the outer surface of the body, the lower surface including an abrasive area capable of scraping an external surface and collecting material scraped from the external surface. The spray canister is disposed within the longitudinal bore of the body. The spray canister includes a reservoir having a self-defense fluid and a nozzle extending outwardly from the opening of the first end of the body. The nozzle is configured to discharge the self-defense fluid upon actuation. The whistle is disposed on the first end of the body over the nozzle and includes a mouthpiece and a safety housing. The housing includes an exit aperture enabling discharge of the fluid from the nozzle and a quick release mechanism removably attaching the housing to the body. The quick release mechanism maintains the spray canister in a fixed position and the nozzle aligned with the exit aperture. The mouthpiece is positioned over the nozzle to prevent inadvertent actuation of the nozzle. The mouthpiece is pivotally connected to the housing enabling pivoting of the mouthpiece about the housing to provide access to the nozzle for actuation. The light source is disposed within the opening of the second end of the body. The light source emanates light outwardly from the second end of the body.

In embodiments, the defense ring includes an interior receptacle disposed between the upper surface and the lower surface of the ring. The interior receptacle can be concave to help retain the collected material scrapped off the external surface. The abrasive area is in communication with the interior receptacle such that material scraped from the external surface may enter the interior receptacle.

In some embodiments, the abrasive area includes a plurality of projections each including a jagged edge and an orifice. The projections extend around the lower surface and protrude outwardly from the lower surface of the defense ring. The orifice enables the ingress of material scraped from the external surface into interior receptacle . . . .

In other embodiments, the mouthpiece is pivotally connected to the housing enabling a downward compression of the mouthpiece to actuate the nozzle and discharge the self-defense fluid.

In embodiments, the body includes a pair of apertures including a first aperture disposed on the first side of the body and a second aperture disposed on the second side of the body. The apertures extend through the body from the outer surface to the interior surface and are positioned adjacent the first end.

In some embodiments, the quick release mechanism of the housing includes a collar having a pair of snap buttons corresponding to the pair of apertures of the body. The pair of snap buttons are configured to removably engage the pair of apertures from within the longitudinal bore to fasten the housing to the body. The housing prevents axial movement of the spray canister within the body when the snap buttons are engaged to the apertures.

In certain embodiments, the collar includes a diameter smaller than a diameter of the longitudinal bore such that the collar fits within the longitudinal bore of the body when the housing is attached to the body.

In other embodiments, the light source is flush with the lower surface of the defense ring.

In embodiments, the light source includes a plurality of flashing light sources operably coupled to a power source, such as a rechargeable power source, is disposed within the longitudinal bore of the body and positioned adjacent to the second end.

In some embodiments, the body includes a third aperture disposed on the body adjacent to the second end. The third aperture extends through the body from the outer surface to the interior surface.

In certain embodiments, the power source is a chargeable battery coupled to a charging port disposed within the third aperture such that the charging port is accessible through the third aperture.

In embodiments, the self-defense device further includes a grip sleeve disposed around the outer surface of the body. The grip sleeve includes a pair of male fasteners corresponding to the pair of apertures of the body that are configured to engage the apertures and fasten the sleeve in position around the body. Multiple sleeves of different colors can be used and interchanged with one another.

In some embodiments, the body includes a recess extending annularly around the first end of the body.

In certain embodiment, the self-defense device includes an accessory clip removably attachable to the recess of the body. The clip includes a fastening collar extending orthogonally outwardly from the clip that engages the recess to fasten the clip to the body. The fastening collar includes a length greater than half of a length of a diameter of the recess, a width less than a width of the recess, and a diameter less than the diameter of the recess, thereby enabling slidable, compressible engagement of the fastening collar around the recess.

The present disclosed technology also provides a method of using a self-defense device to collect deoxyribonucleic acid (DNA) from an attacker including employing a self-defense device including a tubular body including a first end, a second end, an outer surface, an interior surface, a first side, a second side, a longitudinal bore extending from the first end to the second end, and a defense ring extending annularly around the second end of the body, the defense ring including an upper surface, a lower surface, and an interior receptacle disposed between the upper surface and lower surface, the lower surface including an abrasive area capable of scraping a body surface of the attacker to collect material scraped from the body surface, the interior receptacle capable of retaining material scrapped off the external surface, contacting the body surface of the attacker with the abrasive area of the defense ring to scrape the body surface and collect material including DNA, and storing the collected material within the interior receptacle of the defense ring.

"Abrasive" refers to "any material capable of drawing or removing material from a surface". "Scrape" refers to "drawing or removing by virtue of cutting, pulling, brushing, sweeping, puncturing, or scratching." "Fluid" refers to "a solid, liquid, or gas including aerosols." "Actuate" refers to "causing a device, machine, or object to operate." "Axial" refers to "relating the longitudinal or lateral axis of a reference object."

Any device or step to a method described in this disclosure can comprise or consist of that which it is a part of, or the parts which make up the device or step. The term "and/or" is inclusive of the items which it joins linguistically and each item by itself. "Substantially" is defined as "at least 95% of the term being described" and any device or aspect of a device or method described herein can be read as "comprising" or "consisting" thereof.

DETAILED DESCRIPTION OF EMBODIMENTS OF THE DISCLOSED TECHNOLOGY

The present disclosed technology provides a self-defense device, including a tubular body, a spray canister disposed in the body for dispensing a self-defense fluid upon actuation, a whistle removably attachable to the body and coupled to the spray canister, and a light source disposed within the body for emanating light. The body includes a longitudinal bore extending therethrough and a defense ring extending annularly around the body. The defense ring includes a lower surface including an abrasive area capable of scraping an external surface and collecting material scraped or otherwise pulled from the external surface. The spray canister is disposed within the longitudinal bore of the body and includes a nozzle configured to discharge the self-defense fluid upon actuation. The whistle includes a mouthpiece and a housing coupled to the spray canister. The housing includes an exit aperture enabling discharge of the fluid from the nozzle and a quick release mechanism for maintaining the spray canister in a fixed position and the nozzle aligned with the exit aperture. The mouthpiece is pivotally connected to the housing enabling pivoting of the mouthpiece about the housing to provide access to the nozzle for actuation.

Figure 1:
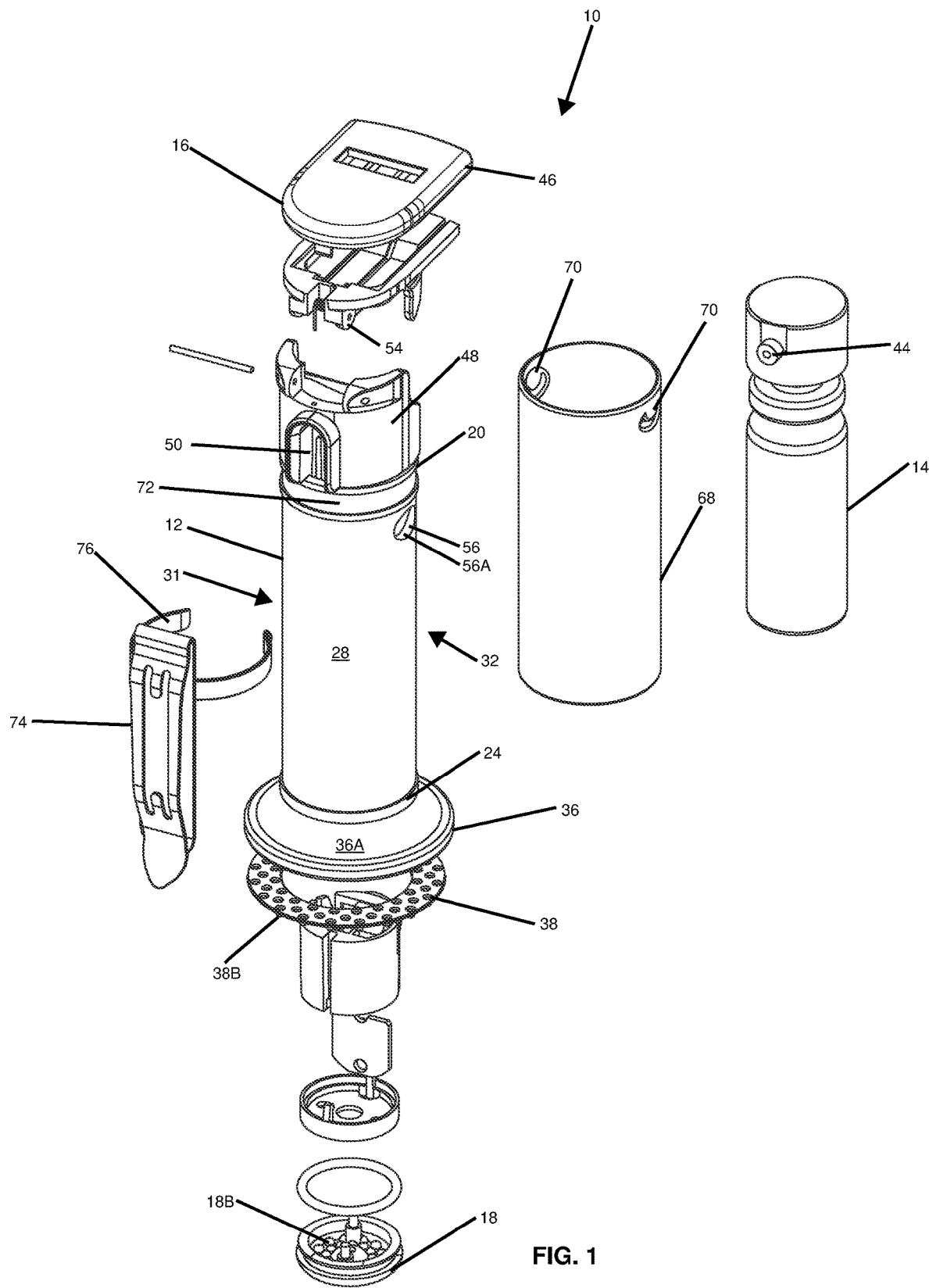
FIG. 1 shows a top exploded view of the self-defense device according to one embodiment of the present disclosed technology.
Figure 2:
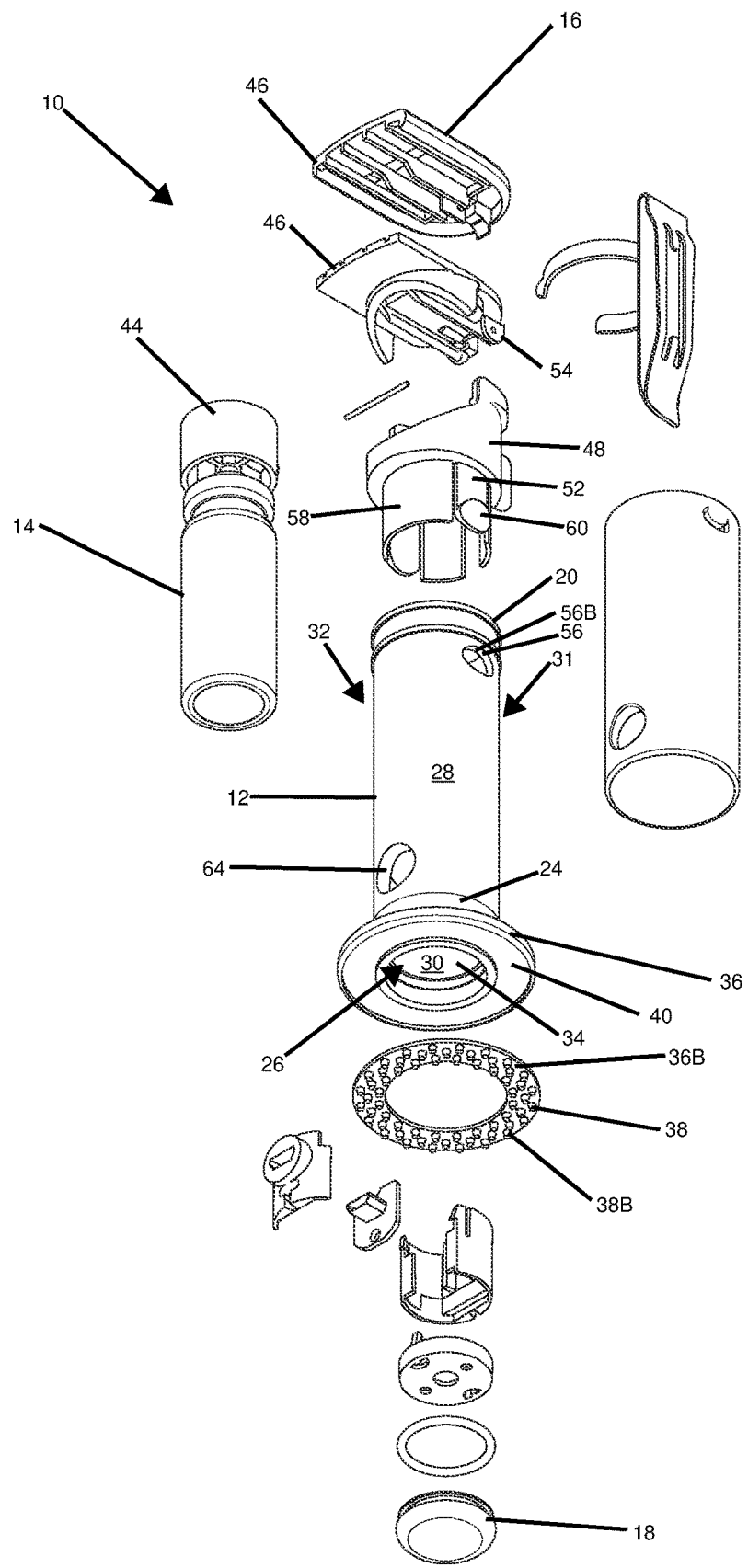
FIG. 2 shows a bottom exploded view of the self-defense device according to one embodiment of the present disclosed technology.
Figure 4:
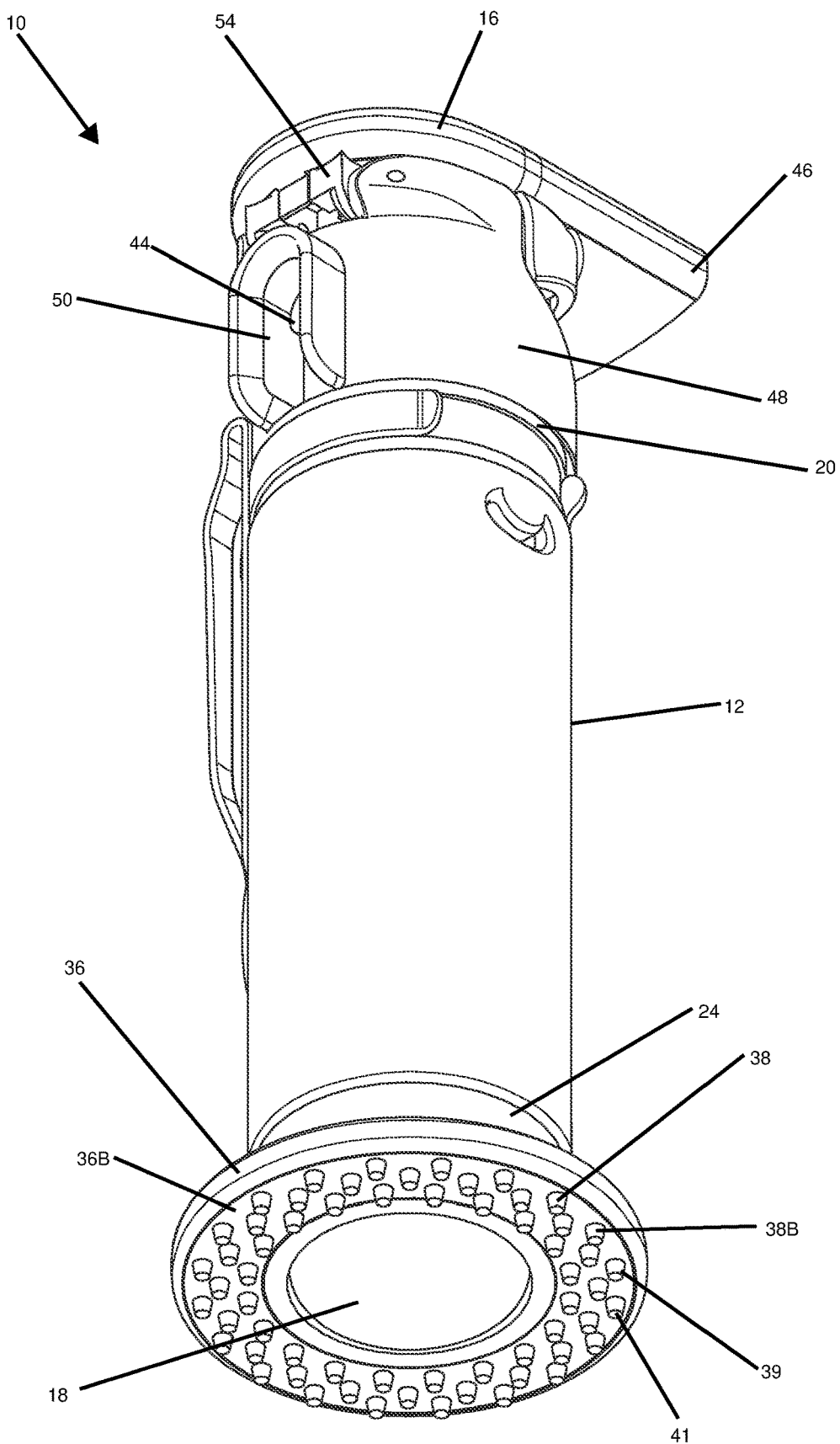
FIG. 4 shows a bottom perspective view of the self-defense device according to one embodiment of the present disclosed technology.

Referring to FIG. 1, FIG. 2, and FIG. 4, simultaneously, FIG. 1 shows a top exploded view of the self-defense device according to one embodiment of the present disclosed technology. FIG. 2 shows a bottom exploded view of the self-defense device according to one embodiment of the present disclosed technology. FIG. 4 shows a bottom perspective view of the self-defense device according to one embodiment of the present disclosed technology. The self-defense device 10 includes a tubular body 12 including a self-defense ring 36 for striking an attacker and collecting DNA therefrom, a spray canister 14 in the body 12 for dispensing a self-defense fluid 43 to disable or dispel the attacker, a whistle 16 coupled to the body 12 and the spray canister 14 for alerting others of an attack, and a light source 18 within the body 12 also for alerting others of an attack.

The tubular body 12 includes a first end 20 having a first opening 22 (see FIG. 6) a second end 24 opposite the first end 20 having a second opening 26, an outer surface 28, an interior surface 30 opposite the outer surface 28, a first side 31, a second side 32 opposite the first side 31, a longitudinal bore 34 extending from the first end 20 to the second end 24, and the defense ring 36.

The ring 36 which extends annularly around the second end 24 of the body 12 and protrudes outwardly relative to the outer surface 28 of the body 12. The ring 36 includes an upper surface 36A and a lower surface 36B opposite the upper surface 36A. The upper surface 36A of the ring 36 is perpendicular to the outer surface 28 of the body 12. The lower surface 36B includes an abrasive area 38 capable of scraping an external surface, such as the body surface of an attacker, and collecting material, such as DNA, i.e., tissue, skin, hair, or blood that is scraped, pulled, or otherwise retrieved from the external surface by the abrasive area 38. In embodiments, the abrasive area 38 comprises a plurality of projections 38B each including a jagged, or sharp, edges 39 to scrap, poke, pull, or otherwise retrieve material from the external surface and an orifice 41. The projections 38B extend around the lower surface 36B and protrude outwardly from the lower surface 36B of the ring 36. The ring 36 includes an interior receptacle 40 capable of retaining the collected material scrapped off the external surface. The orifices 41 are in communication with the interior receptacle 40 to enable the ingress, or the flow, of material scraped from the external surface.

Figure 5:
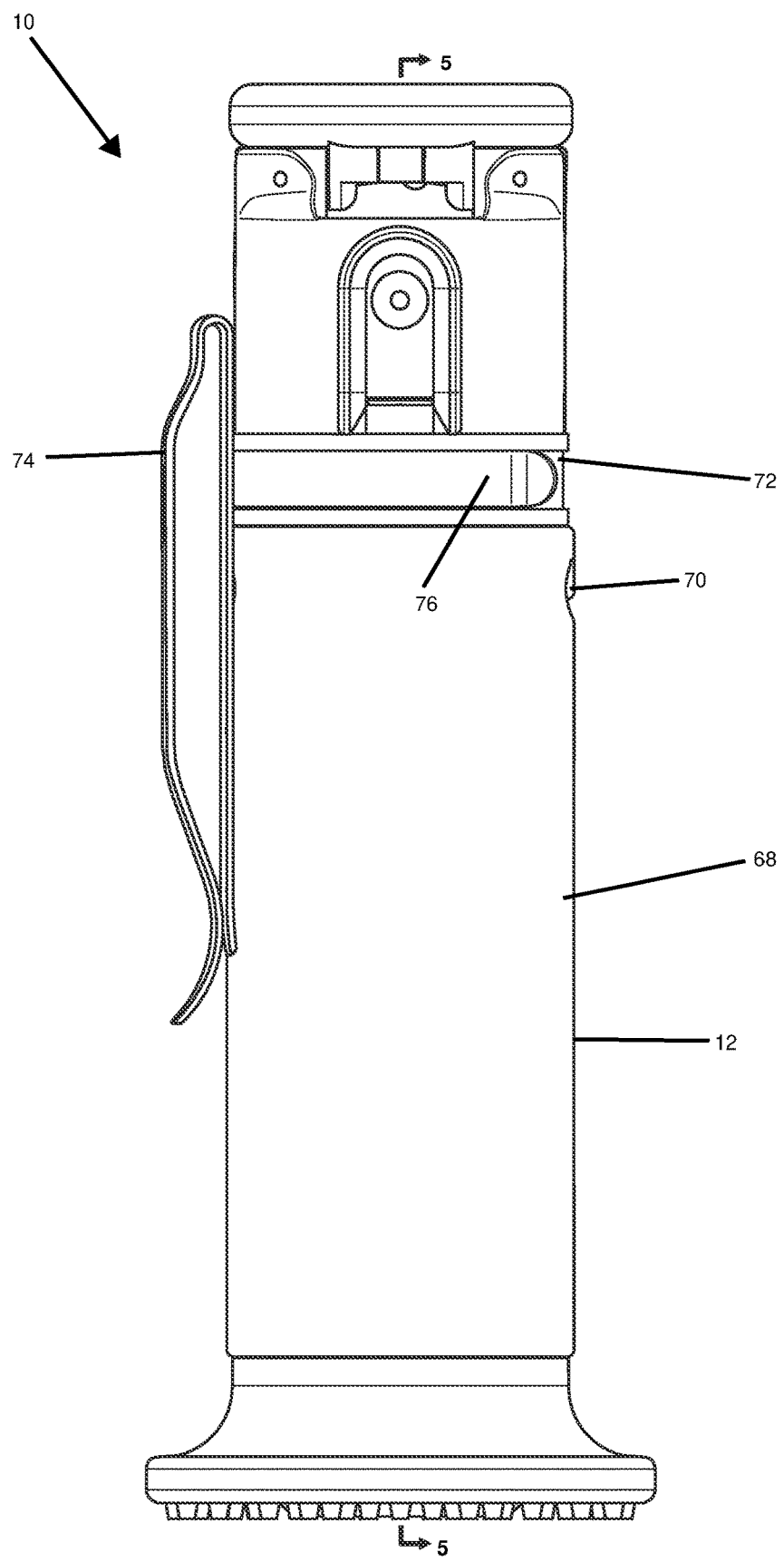
FIG. 5 shows a side view of the self-defense device according to one embodiment of the present disclosed technology.
Figure 6:
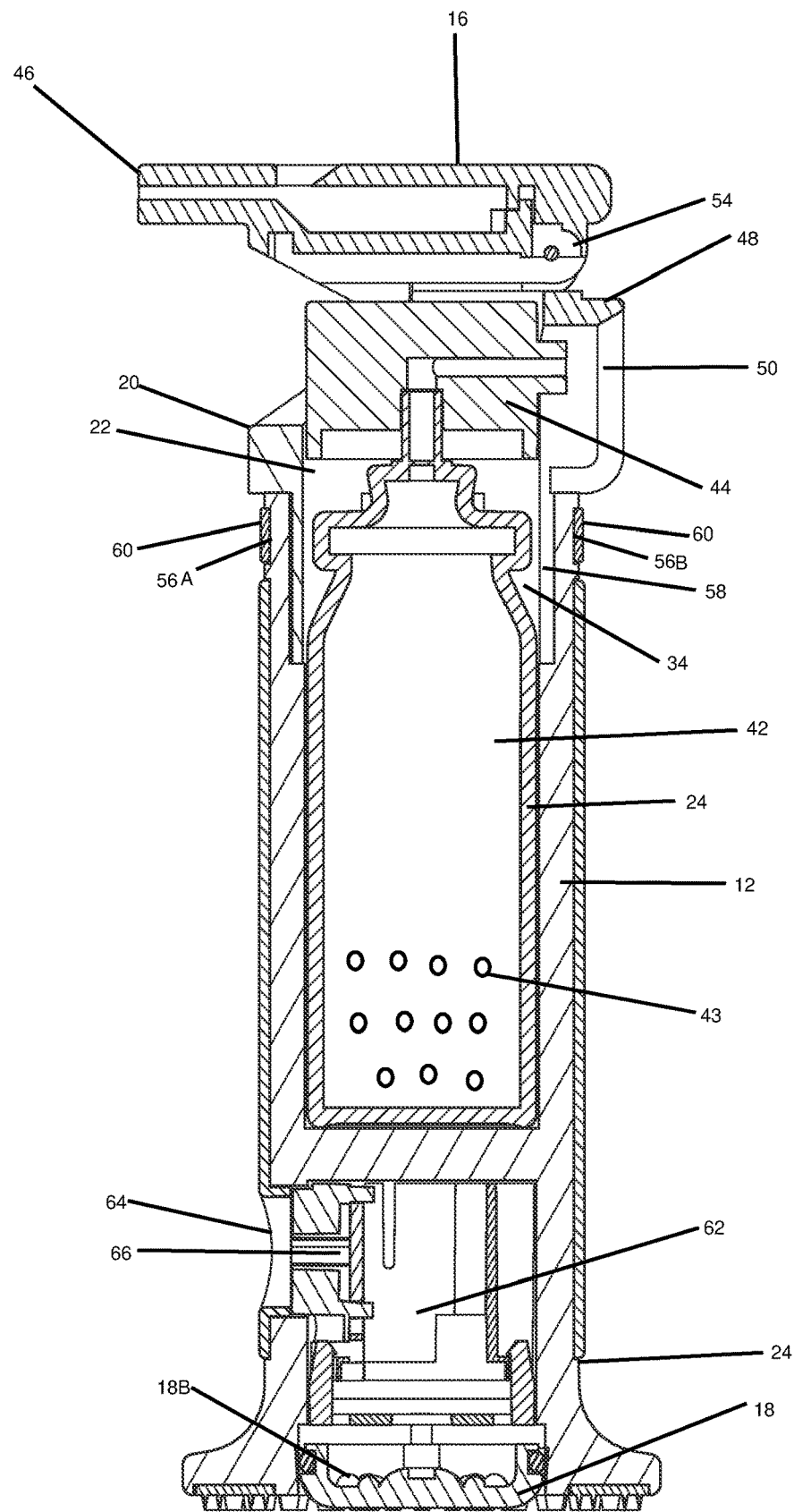
FIG. 6 shows cross-sectional view along line 5-5 of FIG. 5 according to one embodiment of the present disclosed technology.

Referring now to FIG. 6, FIG. 6 shows cross-sectional view along line 5-5 of FIG. 5 according to one embodiment of the present disclosed technology. The spray canister 14 is disposed within the longitudinal bore 34 of the body 12. The spray canister 14 includes a reservoir 42 having a self-defense fluid 43, such as oleoresin capsicum (OC), or pepper spray, and a nozzle 44 extending outwardly from the opening 22 of the first end 20 of the body 12. The nozzle 44 is actuable and configured to discharge the self-defense fluid 43 upon actuation.

Referring again to FIG. 1, FIG. 2 and FIG. 4, in conjunction with FIG. 6, the whistle 16 is disposed on the first end 20 of the body 12 over the nozzle 44. The whistle 16 includes a mouthpiece 46 and a housing 48 having an exit aperture 50 enabling discharge of the self-defense fluid 43 from the nozzle 44. The housing 48 also includes a quick release mechanism 52 for removably attaching the housing 48 to the body 12. The quick release mechanism 52 maintains the spray canister 14 in a fixed position and the nozzle 44 aligned with the exit aperture 50. The mouthpiece 46 is positioned over the nozzle 44 to prevent inadvertent actuation of the nozzle 44 by a user. The mouthpiece 46 extends outwardly from the housing 48 and is positioned opposite the exit aperture 50. The mouthpiece 46 is pivotally connected to the housing 48 via a hinge 54, enabling pivoting of the mouthpiece 46 about the housing 48 to provide access to the nozzle 44 for actuation by the user. In embodiments, the mouthpiece 46 pivots about the housing 48 enabling a downward compression of the mouthpiece 46 to actuate the nozzle 44 and discharge the self-defense fluid 43.

The body 12 further comprises a pair of apertures 56 including a first aperture 56A disposed on the second side 32 and a second aperture 56B disposed on the first side 31. The apertures 56 extend through the body 12 from the outer surface 28 to the interior surface 30 and are positioned adjacent the first end 20 of the body 12. The quick release mechanism 52 of the housing 48 includes a collar 58 having a pair of snap buttons 60 corresponding to the pair of apertures 56 of the body 12. The pair of snap buttons 60 are configured to removably engage the pair of apertures 56 from within the longitudinal bore 34 to fasten the housing 48 to the body 12. The housing 48 via the quick release mechanism 52, prevents axial movement of the spray canister 14 within the body 12 when the snap buttons 60 are engaged to the apertures 56. In embodiments, the collar 58 includes a diameter smaller than a diameter of the longitudinal bore 34 of the body 12 such that the collar 58 fits within the longitudinal bore 34 when the housing 48 is attached to the body 12.

Figure 3:
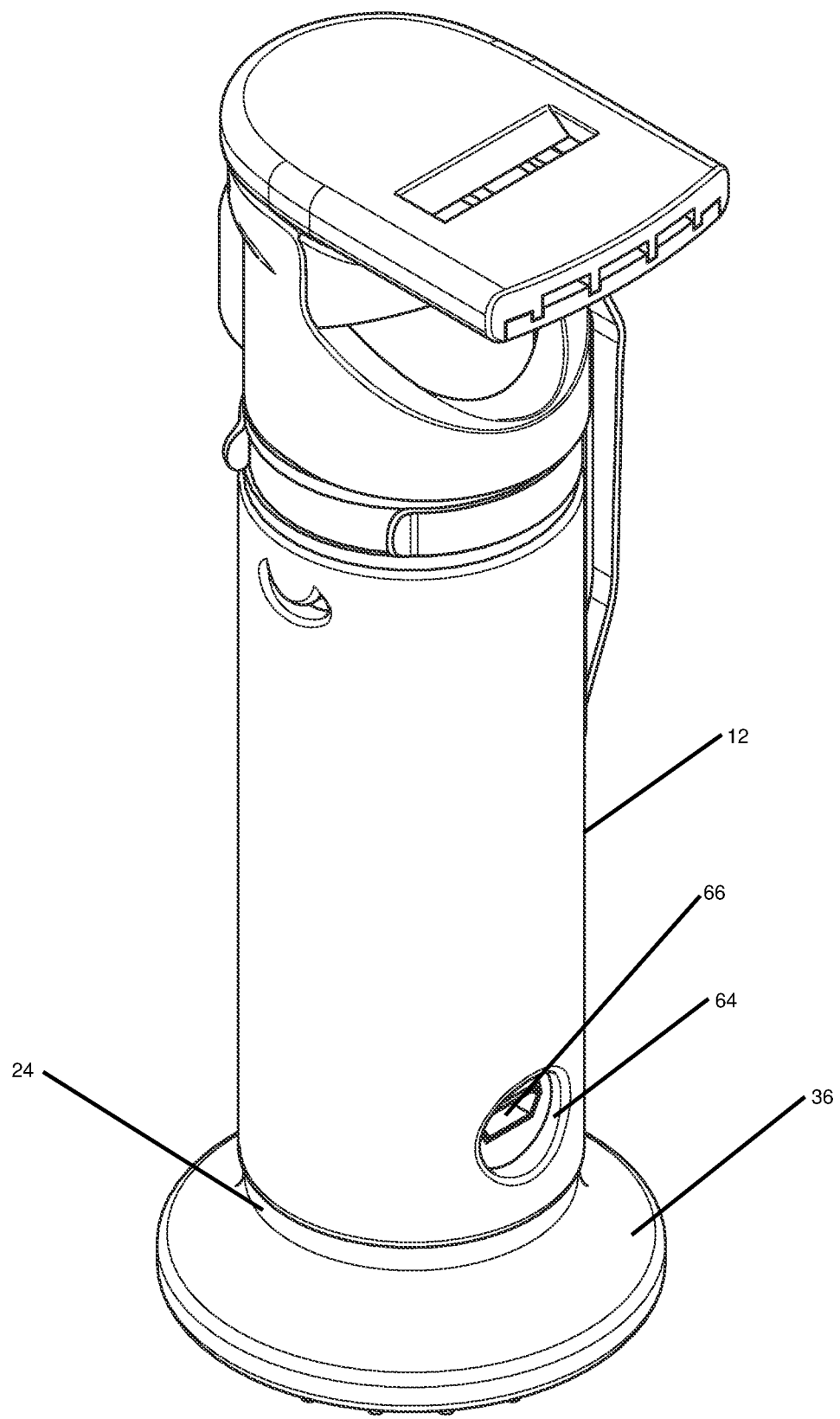
FIG. 3 shows a top perspective view of the self-defense device according to one embodiment of the present disclosed technology.

Referring again to FIG. 1, FIG. 2, and FIG. 6, simultaneously, in conjunction with FIG. 3, FIG. 3 shows a top perspective view of the self-defense device according to one embodiment of the present disclosed technology. The light source 18 is disposed within the opening 26 of the second end 24 of the body 12. The light source 18 emanates light outwardly from the second end 24 to alert others of a potential or ongoing attack. The light source 18 is flush with the lower surface 36B of the ring 36 and includes a plurality of flashing light sources 18B operably coupled to a power source 62 disposed within the longitudinal bore 34 and positioned adjacent to the second end 24 of the body 12.

The body 12 includes a third aperture 64 positioned in between the first side 31 and second side 32 and adjacent to the second end 24. The third aperture 64 extends through the body 12 from the outer surface 28 to the interior surface 30. The power source 62 is a chargeable battery coupled to a charging port 66 disposed within the third aperture 64 such that the charging port 66 is accessible to a user through the third aperture 64.

Referring again to FIG. 1 and FIG. 4, simultaneously, in conjunction with FIG. 5, FIG. 5 shows a side view of the self-defense device according to one embodiment of the present disclosed technology. The self-defense device 10 further comprises a grip sleeve 68 disposed around the outer surface 28 of the body 12. The grip sleeve 68 includes a pair of male fasteners 70 corresponding to the pair of apertures 56 of the body 12. The fasteners 70 are configured to engage the apertures 56 and fasten the sleeve 68 in position around the body 12.

The body 12 includes a recess 72 extending annularly around the first end 20 of the body 12. The grip sleeve 68 extends from the recess to the ring 36.

The self-defense device 10 includes an accessory clip 74 removably attachable to the recess 72. The clip 74 includes a fastening collar 76 extending orthogonally outwardly from the clip 74 that engages the recess 72 to fasten the clip 74 to the body 12. In embodiments, the fastening collar 76 includes a length greater than half of a length of a diameter of the recess 72, a width less than a width of the recess 72, and a diameter less than the diameter of the recess, 72 thereby enabling slidable, compressible engagement of the fastening collar 76 around the recess.

In one operation of the self-defense device, a user may collect DNA from an attacker by contacting the body surface of the attacker with the abrasive area 38 of the defense ring 36. The sharp nature of the plurality of projections 38B will scrap, pull, or otherwise retrieve body material, such as skin, hair, or tissue, from the body surface of the attacker. The collected body material will then be stored within the interior receptacle 40.

Any device or step to a method described in this disclosure can comprise or consist of that which it is a part of, or the parts which make up the device or step. The term "and/or" is inclusive of the items which it joins linguistically and each item by itself.

For purposes of this disclosure, the term "substantially" is defined as "at least 95% of" the term which it modifies.

Any device or aspect of the technology can "comprise" or "consist of" the item it modifies, whether explicitly written as such or otherwise.

When the term "or" is used, it creates a group which has within either term being connected by the conjunction as well as both terms being connected by the conjunction.

While the disclosed technology has been disclosed with specific reference to the above embodiments, a person having ordinary skill in the art will recognize that changes can be made in form and detail without departing from the spirit and the scope of the disclosed technology. The described embodiments are to be considered in all respects only as illustrative and not restrictive. All changes that come within the meaning and range of equivalency of the claims are to be embraced within their scope. Combinations of any of the methods and apparatuses described hereinabove are also contemplated and within the scope of the invention.

What is claimed is:

1. A self-defense device, comprising:
   a tubular body including a first end having a first opening, a second end having a second opening, the first end opposite the second end, an outer surface, an interior surface, the outer surface opposite the interior surface, a first side, a second side, the first side opposite the second side, a longitudinal bore extending from the first end to the second end, and a defense ring extending annularly around the second end of the body and protruding outwardly relative to the body, the defense ring including an upper surface and a lower surface, the upper surface perpendicular to the outer surface of the body, the lower surface including an abrasive area capable of scraping an external surface and collecting material scraped from the external surface;
   a spray canister disposed within the longitudinal bore of the body, the spray canister including a reservoir having a self-defense fluid and a nozzle extending outwardly from the opening of the first end of the body, the nozzle configured to discharge the self-defense fluid upon actuation;
   a whistle disposed on the first end of the body over the nozzle, the whistle including a mouthpiece and a housing, the housing including an exit aperture enabling discharge of the fluid from the nozzle and a quick release mechanism removably attaching the housing to the body, the quick release mechanism maintaining the spray canister in a fixed position and the nozzle aligned with the exit aperture, the mouthpiece positioned over the nozzle to prevent inadvertent actuation of the nozzle, the mouthpiece pivotally connected to the housing enabling pivoting of the mouthpiece about the housing to provide access to the nozzle for actuation; and
   a light source disposed within the opening of the second end of the body, the light source emanating light outwardly from the second end of the body.

2. The self-defense device of claim 1, wherein:
   the defense ring includes an interior receptacle disposed between the upper surface and the lower surface of the ring, the interior receptacle capable of retaining the collected material scrapped off the external surface; and
   the abrasive area is in communication with the receptacle such that material scraped from the external surface may enter the interior receptacle.

3. The self-defense device of claim 2, wherein the abrasive area comprises a plurality of projections each including a jagged edge and an orifice, the projections extending around the lower surface and protruding outwardly from the lower surface of the defense ring, the orifice enabling the ingress of material scraped from the external surface into interior receptacle.

4. The self-defense device of claim 1, wherein the mouthpiece is pivotally connected to the housing enabling a downward compression of the mouthpiece to actuate the nozzle and discharge the self-defense fluid.

5. The self-defense device of claim 1, wherein the body comprises a pair of apertures including a first aperture disposed on the first side and a second aperture disposed on the second side, the apertures extending through the body from the outer surface to the interior surface and positioned adjacent the first end.

6. The self-defense device of claim 5, wherein the quick release mechanism of the housing includes a collar having a pair of snap buttons corresponding to the pair of apertures of the body, the pair of snap buttons configured to removably engage the pair of apertures from within the longitudinal bore to fasten the housing to the body, the housing preventing axial movement of the spray canister within the body when the snap buttons are engaged to the apertures.

7. The self-defense device of claim 6, wherein the collar includes a diameter smaller than a diameter of the longitudinal bore such that the collar fits within the longitudinal bore of the body when the housing is attached to the body.

8. The self-defense device of claim 1, wherein the light source is flush with the lower surface of the defense ring.

9. The self-defense device of claim 8, wherein the light source comprises a plurality of flashing light sources operably coupled to a power source disposed within the longitudinal bore of the body, the power source adjacent to the second end.

10. The self-defense device of claim 9, wherein the body includes a third aperture disposed on the body adjacent to the second end, the third aperture extending through the body from the outer surface to the interior surface.

11. The self-defense device of claim 10, wherein the power source is a chargeable battery coupled to a charging port disposed within the third aperture such that the charging port is accessible through the third aperture.

12. The self-defense device of claim 5, further comprising a grip sleeve disposed around the outer surface of the body, the grip sleeve including a pair of male fasteners corresponding to the pair of apertures of the body that are configured to engage the apertures and fasten the sleeve in position around the body.

13. The self-defense device of claim 1, wherein the body includes a recess extending annularly around the first end of the body.

14. The self-defense device of claim 13, further comprising an accessory clip removably attachable to the recess of the body, the clip including a fastening collar extending orthogonally outwardly from the clip that engages the recess to fasten the clip to the body.

15. The self-defense device of claim 14, wherein the fastening collar includes a length greater than half of a length of a diameter of the recess, a width less than a width of the recess, and a diameter less than the diameter of the recess, thereby enabling slidable, compressible engagement of the fastening collar around the recess.

16. A method of using a self-defense device to collect deoxyribonucleic acid (DNA) from an attacker, comprising:
employing a self-defense device including a tubular body including a first end, a second end, an outer surface, an interior surface, a first side, a second side, a longitudinal bore extending from the first end to the second end, and a defense ring extending annularly around the second end of the body, the defense ring including an upper surface, a lower surface, and an interior receptacle disposed between the upper surface and lower surface, the lower surface including an abrasive area capable of scraping a body surface of the attacker to collect material scraped from a body surface, the interior receptacle capable of retaining material scrapped off the body surface;
contacting the body surface of the attacker with the abrasive area of the defense ring to scrape the body surface and collect material including DNA; and
storing the collected material within the interior receptacle of the defense ring.

17. The method of claim 16, wherein the defense ring protrudes outwardly relative to the body and the upper surface of the defense ring is perpendicular to the outer surface of the body.

18. The method of claim 17, wherein the self-defense device comprises a spray canister disposed within the longitudinal bore of the body, the spray canister including a reservoir having a self-defense fluid and a nozzle extending outwardly from an opening of the first end of the body, the nozzle configured to discharge the self-defense fluid upon actuation.

19. The method of claim 18, wherein the self-defense device further comprises a whistle disposed on the first end of the body over the nozzle, the whistle including a mouthpiece and a housing, the housing including an exit aperture enabling discharge of the fluid from the nozzle and a quick release mechanism removably attaching the housing to the body, the quick release mechanism maintaining the spray canister in a fixed position and the nozzle aligned with the exit aperture, the mouthpiece positioned over the nozzle to prevent inadvertent actuation of the nozzle, the mouthpiece pivotally connected to the housing enabling pivoting of the mouthpiece about the housing to provide access to the nozzle.

20. The method of claim 19, wherein the self-defense device further comprises a light source disposed within an opening of the second end of the body, the light source emanating light outwardly from the second end of the body.

* * * * *